US012203466B2

(12) United States Patent
Ishizaki et al.

(10) Patent No.: US 12,203,466 B2
(45) Date of Patent: Jan. 21, 2025

(54) DIAPHRAGM PUMP AND BLOOD PURIFICATION APPARATUS USING SAME

(71) Applicant: Nikkiso Company Limited, Tokyo (JP)

(72) Inventors: Fumihiko Ishizaki, Tokyo (JP); Yuya Menjoh, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 223 days.

(21) Appl. No.: 17/617,289

(22) PCT Filed: Jun. 5, 2020

(86) PCT No.: PCT/JP2020/022390
§ 371 (c)(1),
(2) Date: Dec. 7, 2021

(87) PCT Pub. No.: WO2020/250835
PCT Pub. Date: Dec. 17, 2020

(65) Prior Publication Data
US 2022/0228586 A1 Jul. 21, 2022

(30) Foreign Application Priority Data
Jun. 12, 2019 (JP) .................. 2019-109370

(51) Int. Cl.
*F04B 43/067* (2006.01)
*F04B 43/073* (2006.01)

(52) U.S. Cl.
CPC .......... *F04B 43/067* (2013.01); *F04B 43/073* (2013.01)

(58) Field of Classification Search
CPC ...... F04B 43/067; F04B 43/073; F04B 43/06; A61M 1/14; A61M 1/367; A61M 60/109;
(Continued)

(56) References Cited

U.S. PATENT DOCUMENTS 4,474,540 A * 10/1984 Bonastia ............... F04B 43/067
417/63
4,634,430 A * 1/1987 Polaschegg ......... A61M 60/837
604/141
(Continued)

FOREIGN PATENT DOCUMENTS

JP S60-259781 A 12/1985
JP S614998 A 1/1986
(Continued)

OTHER PUBLICATIONS

Notice from the Japan Patent Office for Application No. 2019-109370, dated Feb. 16, 2022, with English translation of art submission by nameless third party.
(Continued)

*Primary Examiner* — Bryan M Lettman
(74) *Attorney, Agent, or Firm* — Young Basile Hanlon & MacFarlane, P.C.

(57) ABSTRACT

A diaphragm pump, includes a case, a diaphragm dividing a space in the case into a first space and a second space, a liquid feed flow path including an inflow path to introduce a liquid to be fed into the first space and an outflow path to discharge the liquid to be fed from the first space, a drive unit including a compression/decompression device that repeatedly causes displacement of the diaphragm by repeating compression and decompression of a driving fluid filling the second space, and a valve mechanism to open and close the inflow path and the outflow path. The drive unit includes a pressure release mechanism to release pressure of the driving fluid after the driving fluid is compressed or decompressed by the compression/decompression device.

7 Claims, 5 Drawing Sheets

(58) Field of Classification Search
CPC .. A61M 60/268; A61M 60/37; A61M 60/427;
A61M 60/538
See application file for complete search history.

(56) References Cited

U.S. PATENT DOCUMENTS

| | | | | |
|---|---|---|---|---|
| 6,481,982 | B1* | 11/2002 | Yokomichi | F04B 43/0081 251/30.01 |
| 6,554,578 | B1* | 4/2003 | Siegel | F04B 43/0081 417/383 |
| 6,604,908 | B1* | 8/2003 | Bryant | A61M 1/362265 417/27 |
| 8,642,088 | B2 | 2/2014 | Reed et al. | |
| 8,960,010 | B1* | 2/2015 | Crnkovich | A61M 1/16 73/714 |
| 9,545,423 | B2 | 1/2017 | Reed et al. | |
| 9,757,505 | B2 | 9/2017 | Lindley et al. | |
| 9,833,554 | B2 | 12/2017 | Crnkovich et al. | |
| 10,104,888 | B2 | 10/2018 | Reed et al. | |
| 10,398,826 | B2 | 9/2019 | Lindley et al. | |
| 10,441,704 | B2 | 10/2019 | Crnkovich et al. | |
| 10,775,252 | B2 | 9/2020 | Funamura et al. | |
| 10,912,876 | B2 | 2/2021 | Crnkovich et al. | |
| 2005/0069425 | A1* | 3/2005 | Gray | F04B 43/067 417/390 |
| 2007/0179422 | A1 | 8/2007 | Schnell et al. | |
| 2011/0059162 | A1 | 3/2011 | Reed et al. | |
| 2014/0134238 | A1 | 5/2014 | Reed et al. | |
| 2015/0314058 | A1* | 11/2015 | O'Mahony | F04B 49/002 417/63 |
| 2016/0089484 | A1 | 3/2016 | Lindley et al. | |
| 2016/0228631 | A1 | 8/2016 | Crnkovich et al. | |
| 2017/0142967 | A1 | 5/2017 | Reed et al. | |
| 2017/0218943 | A1* | 8/2017 | Ellis | F04B 51/00 |
| 2017/0340798 | A1 | 11/2017 | Lindley et al. | |
| 2018/0093033 | A1 | 4/2018 | Crnkovich et al. | |
| 2019/0336673 | A1 | 11/2019 | Crnkovich et al. | |

FOREIGN PATENT DOCUMENTS

| | | |
|---|---|---|
| JP | 2003-033430 A | 2/2003 |
| JP | 2005-253555 A | 9/2005 |
| JP | 2017-504389 A | 2/2017 |
| JP | 2017-529126 A | 10/2017 |
| JP | 2018-068779 A | 5/2018 |
| JP | 6483874 B1 | 3/2019 |

OTHER PUBLICATIONS

"Documents of Submission Form of Publications, etc." for Application No. 2019-109370, dated Jan. 27, 2022, with English translation.
European Search Report for Application No. 20822133.3, dated Nov. 16, 2022, 7 pgs.
Japanese Office Action for Application No. 2019-109370, dated Oct. 18, 2022, with English translation, 13 pages.
Chinese First Office Action for Application No. 202080042817.9, dated Jan. 11, 2023, with English translation, 20 pgs.
Potentially related to U.S. Appl. No. 17/311,058, filed Jun. 4, 2021.
International Search Report for Application No. PCT/JP2020/022390, dated Jul. 28, 2020.

* cited by examiner

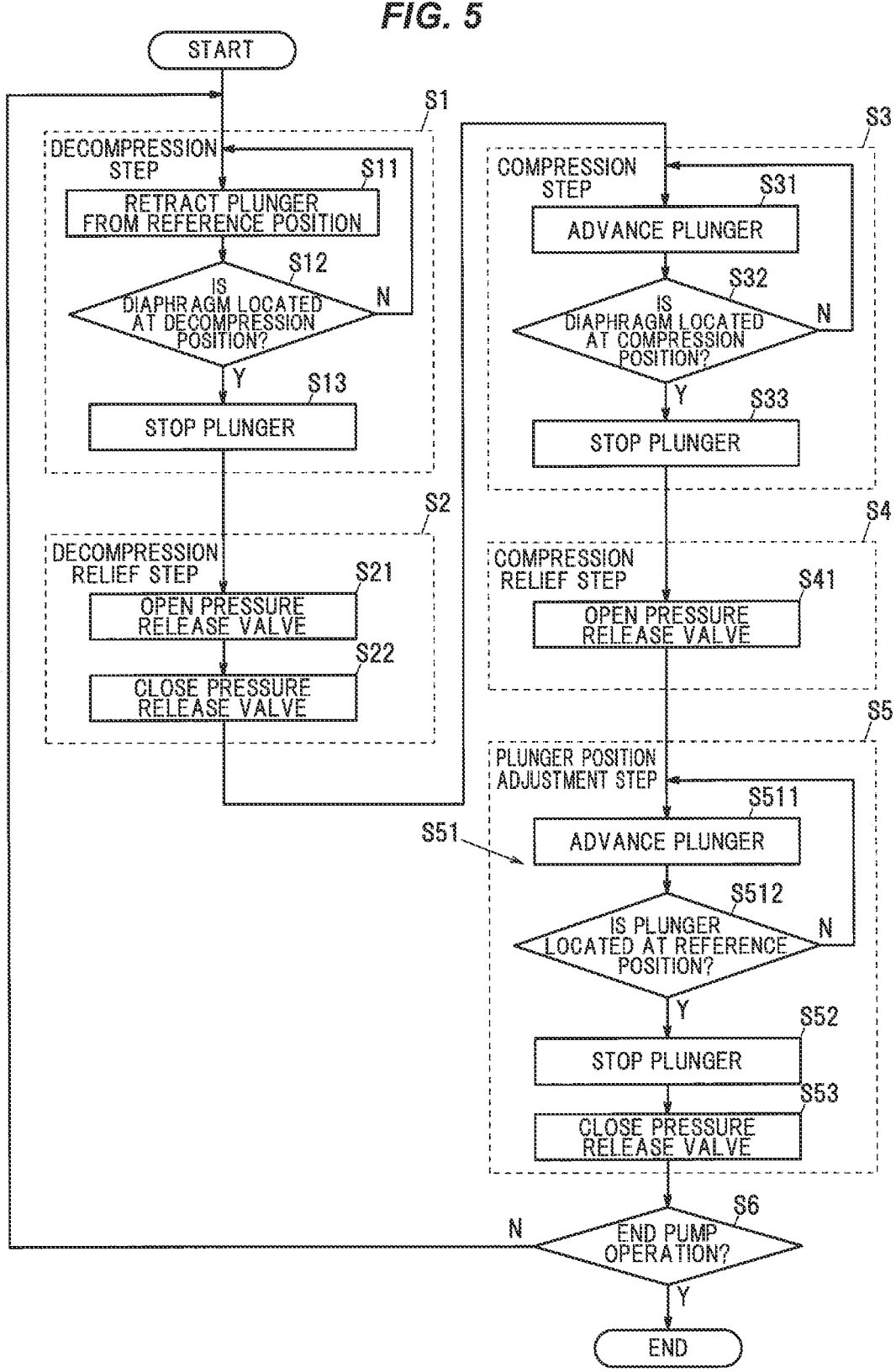

DIAPHRAGM PUMP AND BLOOD PURIFICATION APPARATUS USING SAME

TECHNICAL FIELD

The present invention relates to a diaphragm pump and a blood purification apparatus using the same.

BACKGROUND ART

Diaphragm pumps perform pump operation by displacing a diaphragm, which is a flexible membrane, in a case and thereby changing a volume of a space in the case (referred to as a first space) through which a liquid to be fed passes. Drive sources to displace the diaphragm include a mechanically-driven type (cam type, solenoid type, etc.), an electrically-driven type (piezoelectric element, etc.), a hydraulic drive, and a pneumatic drive.

In, e.g., hydraulically-driven or pneumatically-driven diaphragm pumps, a diaphragm is displaced by compressing or decompressing a driving fluid filling a space separated from the first space by the diaphragm in the case (referred to as a second space) (see, e.g., Patent Literature 1).

CITATION LIST

Patent Literature

Patent Literature 1: Japanese published examined application No. 61-4998

SUMMARY OF INVENTION

Technical Problem

The present inventors conceived of using a diaphragm pump as a liquid feed pump of a blood purification apparatus. The diaphragm pump is desired to be as compact as possible to avoid an increase in size of the blood purification apparatus.

Therefore, it is an object of the invention to provide a compact diaphragm pump and a blood purification apparatus using the same.

Solution to Problem

To solve the problem mentioned above, the invention provides a diaphragm pump, comprising:
a case;
a diaphragm dividing a space in the case into a first space and a second space;
a liquid feed flow path comprising an inflow path to introduce a liquid to be fed into the first space and a outflow path to discharge the liquid to be fed from the first space;
a drive unit comprising a compression/decompression device that repeatedly causes displacement of the diaphragm by repeating compression and decompression of a driving fluid filling the second space; and
a valve mechanism to open and close the inflow path and the outflow path,
wherein the drive unit comprises a pressure release mechanism to release pressure of the driving fluid after the driving fluid is compressed or decompressed by the compression/decompression device.

To solve the problem mentioned above, the invention also provides a blood purification apparatus, comprising:

a blood circuit to extracorporeally circulate blood of a patient;
a liquid supply flow path to supply a supply liquid to the blood circuit or to a blood purifier provided on the blood circuit, and
a waste liquid flow path to discharge a waste liquid from the blood purifier,
wherein at least one of liquid feed pumps provided on the blood circuit, the liquid supply flow path and the waste liquid flow path comprises the diaphragm pump described above.

Advantageous Effects of Invention

According to the invention, it is possible to provide a compact diaphragm pump and a blood purification apparatus using the same.

BRIEF DESCRIPTION OF DRAWINGS

FIG. 5 is a flowchart showing a modification of the control flow executed by the control unit.

DESCRIPTION OF EMBODIMENTS

Embodiment

Figure 1:
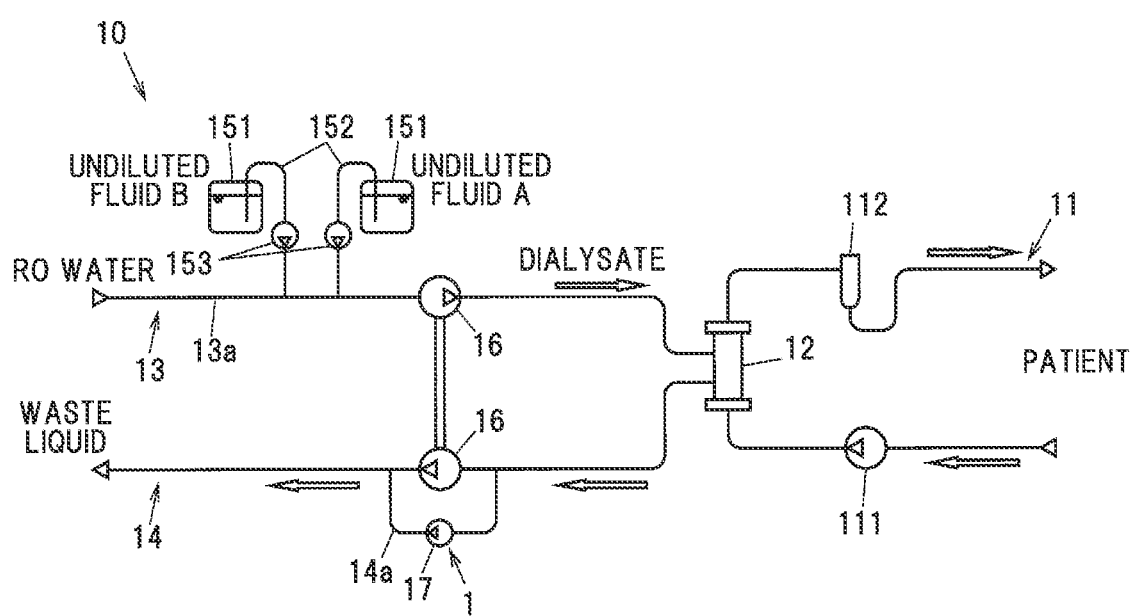
FIG. 1 is a schematic configuration diagram illustrating a blood purification apparatus in an embodiment of the present invention.

An embodiment of the invention will be described below in conjunction with the appended drawings.
(Blood Purification Apparatus)
Firstly, a blood purification apparatus in which a diaphragm pump of the present embodiment is used will be described. FIG. 1 is a schematic configuration diagram illustrating a blood purification apparatus in the present embodiment.

As shown in FIG. 1, a blood purification apparatus 10 includes a liquid supply flow path 13 to supply a supply liquid to a blood circuit 11 extracorporeally circulating blood of a patient or to a blood purifier 12 provided on the blood circuit 11, and a waste liquid flow path 14 to discharge a waste liquid from the blood purifier 12. FIG. 1 shows an example in which the liquid supply flow path 13 is a dialysate flow path 13a to supply a dialysate to the blood purifier 12. However, it is not limited thereto, and the liquid supply flow path 13 may be a replenishing liquid flow path to supply a replenishing liquid directly to the blood circuit 11, or may include both the dialysate flow path 13a and the replenishing liquid flow path.

The blood circuit 11 is composed of, e.g., a flexible tube, etc. A blood pump 111, the blood purifier 12 and a gas-liquid separator 112 are sequentially provided on the blood circuit 11 from the upstream to the downstream of a blood flow. The blood pump 111 is a liquid feed pump to send blood. The gas-liquid separator 112 is a device to remove air bubbles from the blood.

From a RO (Reverse Osmosis) device (not shown) which produces clean water (referred to as dialysis water) using a reverse osmosis membrane (RO membrane), dialysis water is supplied to the dialysate flow path 13*a*. Two types of undiluted dialysate fluids, an undiluted fluid A and an undiluted fluid B, are also supplied to the dialysate flow path 13*a*. The two undiluted fluids are respectively stored in undiluted fluid storage tanks 151, and the undiluted fluid A and the undiluted fluid B are supplied to the dialysate flow path 13*a* respectively from the undiluted fluid storage tanks 151 via undiluted fluid flow paths 152. Undiluted fluid injection pumps 153, which are liquid feed pumps pumping out the undiluted fluid A or the undiluted fluid B, are respectively provided on the two undiluted fluid flow paths 152. The undiluted fluid A and the undiluted fluid B are mixed with the dialysis water in the dialysate flow path 13*a* and the dialysate is thereby prepared. The prepared dialysate is introduced into the blood purifier 12 via a duplex pump 16.

The waste liquid from the blood purifier 12 is discharged through the waste liquid flow path 14. The duplex pump 16 is provided over the dialysate flow path 13*a* and the waste liquid flow path 14 and performs pump operation so that an amount of the dialysate introduced into the blood purifier 12 is equal to an amount of the waste liquid discharged from the blood purifier 12. In addition, a water removal flow path 14*a* is provided on the waste liquid flow path 14 so as to bypass the dual pump 16, and a water removal pump 17 is provided on the water removal flow path 14*a*. When the water removal pump 17 is driven, the amount of the waste liquid discharged from the blood purifier 12 becomes larger than the amount of the dialysate introduced into the blood purifier 12 and water is removed from the blood. It is possible to adjust the amount of water removed from the blood by adjusting the amount of liquid sent by the water removal pump 17.

In the blood purification apparatus 10 of the present embodiment, a diaphragm pump 1 of the invention is used as at least one of liquid feed pumps provided on the blood circuit 11, the liquid supply flow path 13 (the dialysate flow path 13*a* in this example) and the waste liquid flow path 14. Although FIG. 1 shows an example in which the diaphragm pump 1 is used as the water removal pump 17, it is not limited thereto. The diaphragm pump 1 can be used as the other liquid feed pump such as the blood pump 111, the undiluted fluid injection pump 153 or the duplex pump 16.

The configuration of FIG. 1 is only an example and a specific configuration of the blood purification apparatus 10 can be changed appropriately.

(Diaphragm Pump 1)

Figure 2A:
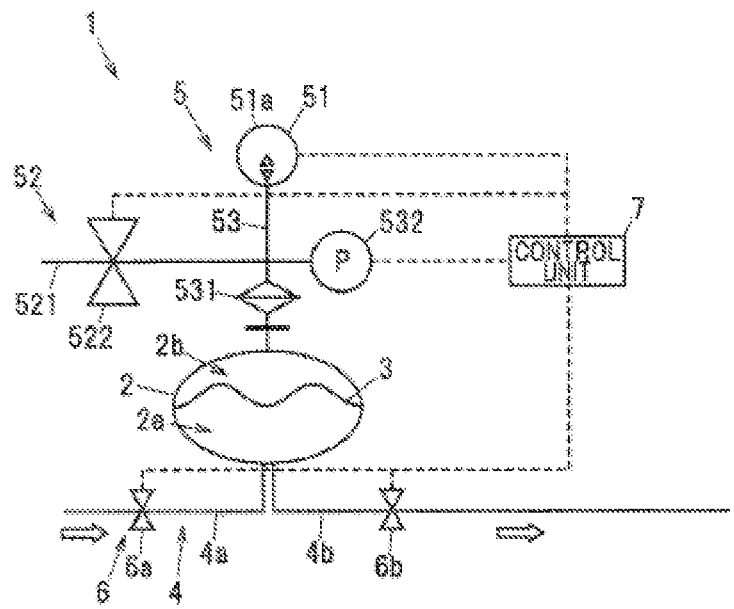
FIG. 2A is a schematic configuration diagram illustrating a diaphragm pump in the embodiment of the invention.
Figure 2B:
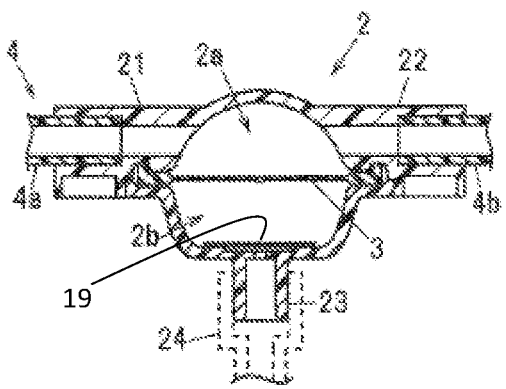
FIG. 2B is a cross-sectional view showing a case.
Figure 2C:
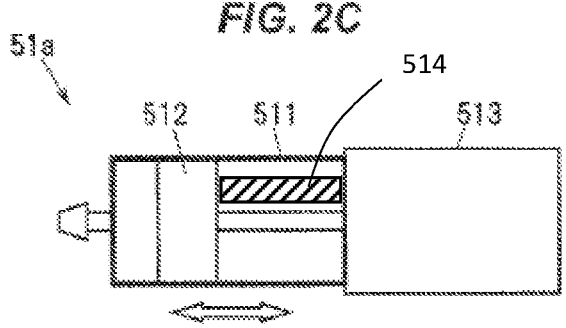
FIG. 2C is a schematic configuration diagram illustrating a reciprocating pump.

FIG. 2A is a schematic configuration diagram illustrating the diaphragm pump 1 in the present embodiment, FIG. 2B is a cross-sectional view showing a case, and FIG. 2C is a schematic configuration diagram illustrating a reciprocating pump. As shown in FIGS. 2A to 2C, the diaphragm pump 1 includes a case 2, a diaphragm 3 dividing a space in the case 2 into a first space 2*a* and a second space 2*b*, a liquid feed flow path 4 having an inflow path 4*a* to introduce a liquid to be fed (the waste liquid in case of the water removal pump 17) into the first space and a outflow path 4*b* to discharge the liquid to be fed from the first space 2*a*, a drive unit 5 to repeatedly cause displacement of the diaphragm 3 by repeating compression and decompression of a driving fluid filling the second space 2*b*, a valve mechanism 6 capable of opening and closing the inflow path 4*a* and the outflow path 4*b*, and a control unit 7.

The case 2 is composed of a hard resin molded article, etc. The case 2 integrally includes a first connection part 21 being in communication with the first space 2*a* and connected to the inflow path 4*a* and a second connection part 22 being in communication with the first space 2*a* and connected to the outflow path 4*b*. The case 2 also integrally includes a protruding part 23 that is in communication with the second space 2*b* and protrudes outward. The diaphragm pump 1 also includes a socket part 24 which is provided separately from the case 2 and into which the protruding part 23 is inserted and connected. Although it is not shown, a driving flow path 53 (described later) is connected to the socket part 24, and the driving flow path 53 is communicated with the second space 2*b* by inserting and connecting the protruding part 23 to the socket part 24. The case 2 is configured to be removable from the socket part 24 by detaching the protruding part 23 from the socket part 24, which allows the case 2 to be disposable. In this regard, the case 2 does not need to be entirely disposable and may be configured to be splittable on, e.g., the second space 2*b* side relative to the diaphragm 3 so that only a portion of the case 2 including the first space 2*a* can be disposable. It is not necessary to separately form the case 2 and the socket part 24, and the case 2 may be integrally formed with the socket part 24.

The diaphragm 3 is a flexible membrane and is provided in the case 2 so as to divide an internal space of the case 2 into two spaces, the first space 2*a* and the second space 2*b*. Materials of the case 2 and the diaphragm 3 are not specifically limited.

The inflow path 4*a* and the outflow path 4*b* are in communication with the first space 2*a* of the case 2. However, it is not limited thereto. It may be configured such that the inflow path 4*a* and the outflow path 4*b* are connected and a connection flow path extending from the connected portion therebetween is in communication with the first space 2*a* of the case 2. In this case, the case 2 needs to have only one connection port to the first space 2*a* and it is thus possible to reduce the number of components such as sealing member and to reduce the cost.

An inflow-side solenoid valve 6*a* capable of opening and closing the inflow path 4*a* is provided on the inflow path 4*a*. An outflow-side solenoid valve 6*b* is provided on the outflow path 4*b*. The inflow-side solenoid valve 6*a* and the outflow-side solenoid valve 6*b* constitute the valve mechanism 6 and are controlled to be opened and closed by the control unit 7.

The valve mechanism 6 is controlled by the control unit 7 to open and close the inflow path 4*a* and the outflow path 4*b* according to displacement of the diaphragm 3. In more detail, by opening the inflow-side solenoid valve 6*a* and closing the outflow-side solenoid valve 6*b* in a decompression step and a compression relief step described later, the liquid to be fed is introduced (sucked) into the first space 2*a* from the inflow path 4*a*. On the other hand, by closing the inflow-side solenoid valve 6*a* and opening the outflow-side solenoid valve 6*b* in a compression step and a decompression relief step described later, the liquid to be fed is sent out from the first space 2*a* to the outflow path 4*b*. The liquid is fed by repeating this operation.

The drive unit 5 has a compression/decompression device 51 and a pressure release mechanism 52. The compression/decompression device 51 repeatedly causes displacement of the diaphragm 3 by repeating compression and decompression of the driving fluid filling the second space 2b. In the present embodiment, a reciprocating pump 51a is used as the compression/decompression device 51.

The reciprocating pump 51a is also called a plunger pump or a piston pump, and has a cylinder 511 in communication with the second space 2b via the driving flow path 53, a plunger 512 (or a piston) provided so as to be able to advance and retract within the cylinder 511, and a plunger driving part 513 to advance and retract the plunger 512.

A positive and negative pressure source such as compressor or vacuum generator can be used as the compression/decompression device 51, but in this case, a regulator to control the pressure or a flow path switching mechanism needs to be provided and the system configuration thus becomes complicated and large and operating sound is also loud. Meanwhile, a peristaltic pump configured to squeeze a tube can be also used as the compression/decompression device 51, but as compared to the reciprocating pump 51a which is used as the compression/decompression device 51 in the present embodiment, a worn part needs to be replaced since the squeezed tube deteriorates over time or operating sound from the squeezed part is loud. By using the reciprocating pump 51a as the compression/decompression device 51, the size can be small with a simple system configuration and the operating noise can also be reduced.

The second space 2b, the driving flow path 53 and the cylinder 511 are filled with the driving fluid and it is possible to compress/decompress the driving fluid by advancing/retracting the plunger 512 within the cylinder 511 by the plunger driving part 513 of the reciprocating pump 51a. In the present embodiment, air is used as the driving fluid. As the plunger driving part 513, it is possible to use, e.g., a stepping motor.

The pressure release mechanism 52 is to release pressure of the driving fluid (to bring the pressure closer to the atmospheric pressure) after the driving fluid is compressed or decompressed by the reciprocating pump 51a as the compression/decompression device 51. The pressure release mechanism 52 has a pressure release flow path 521 with one end in communication with the second space 2b and the other end opened to the atmosphere, and a pressure release valve 522 provided on the pressure release flow path 521 to open/close the pressure release flow path 521. In the example shown in the drawing, the pressure release flow path 521 is connected at one end to the driving flow path 53 and is in communication with the second space 2b via the driving flow path 53.

In the present embodiment, the other end of the pressure release flow path 521 is opened to the atmosphere since air is used as the driving fluid. In this regard, when a liquid is used as the driving fluid, the other end of the pressure release flow path 521 should be connected to a container for storing this liquid. The container for storing the liquid may be opened to the atmosphere or may be, e.g., expandable and contractable in a balloon like manner. However, since use of a liquid as the driving fluid makes handling difficult, it is more desirable to use the air as the driving fluid. In addition, the pressure to which the driving fluid is released is the atmospheric pressure in the present embodiment, but it is not limited thereto. The pressure to which the driving fluid is released may not be the atmospheric pressure.

An air filter 531 is provided in the driving flow path 53. The air filter 531 is a so-called hydrophobic filter, and is configured to allow gases to pass therethrough but to not allow liquids to pass therethrough (very high resistance to the passage of liquids). Furthermore, a pressure sensor 532 to measure the pressure of the driving fluid is provided on the driving flow path 53 on the reciprocating pump 51a side relative to the air filter 531. In the event that, e.g., the liquid to be fed leaks to the second space 2b due to damage on the diaphragm 3, etc., the air filter 531 gets wet and pressure of the driving fluid when performing compression by the reciprocating pump 51a becomes higher. Thus, the control unit 7 can detect failure of the diaphragm pump 1 by determining whether an output value of the pressure sensor 532 is more than a predetermined threshold.

In addition to the failure detection mentioned above, the control unit 7 controls opening and closing of the valve mechanism 6, driving of the reciprocating pump 51a as the compression/decompression device 51, and opening and closing of the pressure release valve 522 of the pressure release mechanism 52. The control unit 7 is realized by appropriately combining an arithmetic element such as CPU, a storage device such as memory, a software, and an interface, etc.

Figure 3:
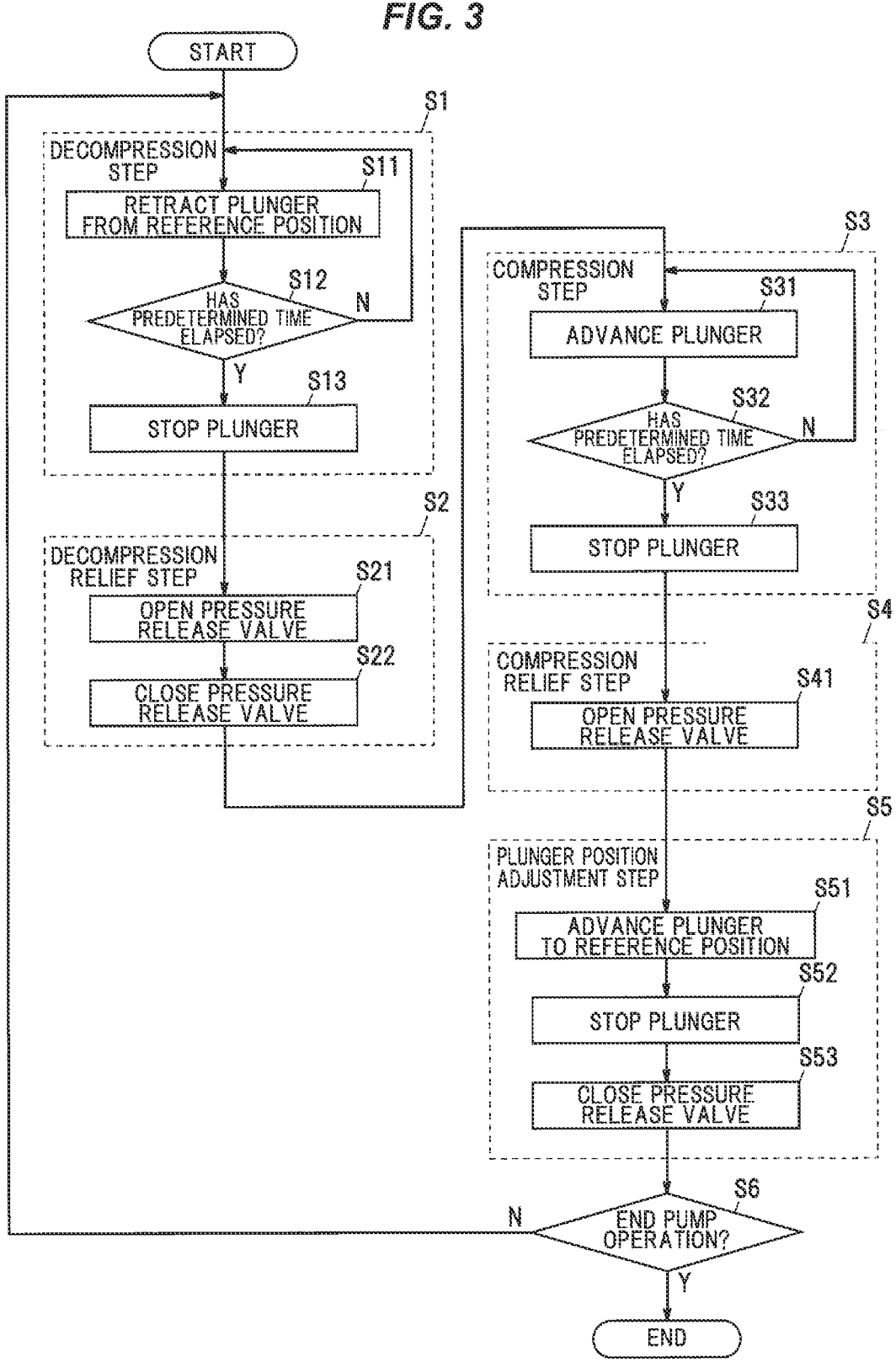
FIG. 3 is a flowchart showing a control flow executed by a control unit.

Next, the drive control of the reciprocating pump 51a and the opening/closing control of the pressure release valve 522 by the control unit 7 will be described. As shown in FIG. 3, the control unit 7 sequentially and repeatedly performs a decompression step (Step S1), a decompression relief step (Step S2), a compression step (Step S3), a compression relief step (Step S4), and a plunger position adjustment step (Step S5).

In the decompression step of Step S1, the plunger 512 is firstly retracted from a reference position in Step S11, and whether a predetermined time has elapsed is determined in Step S12. When the determination made in Step S12 is No, the process returns to Step S11. When the determination made in Step S12 is Yes, the plunger 512 is stopped in Step S13. The reference position in the present embodiment is a position of the plunger 512 when fully pushed (the most advanced position). By performing the decompression step, the driving fluid is decompressed and the diaphragm 3 is displaced such that the volume of the first space 2a increases. At this time, the control unit 7 opens the inflow-side solenoid valve 6a and closes the outflow-side solenoid valve 6b, and the liquid to be fed is thereby introduced (sucked) into the first space 2a from the inflow path 4a.

In the decompression relief step of Step S2, after the driving fluid is released to the atmospheric pressure by opening the pressure release valve 522 in Step S21, the pressure release valve 522 is closed in Step S22. Since pressure of the driving fluid becomes the atmospheric pressure by performing the decompression relief step, the diaphragm 3 returns to a no-load position. Before opening the pressure release valve 522 in Step S21, the control unit 7 closes the inflow-side solenoid valve 6a and opens the outflow-side solenoid valve 6b so that the liquid to be fed does not flow back. In this regard, the outflow-side solenoid valve 6b may be closed.

In the compression step of Step S3, the plunger 512 is advanced in Step S31, and whether a predetermined time has elapsed is determined in Step S32. When the determination made in Step S32 is No, the process returns to Step S31. When the determination made in Step S32 is Yes, the plunger 512 is stopped in Step S33. By performing the compression step, the driving fluid is compressed and the diaphragm 3 is displaced such that the volume of the first space 2a decreases. At this time, the control unit 7 maintains the state in which the inflow-side solenoid valve 6a is close and the outflow-side solenoid valve 6b is open, and the liquid to be fed is thereby sent out from the first space 2a to the outflow path 4b.

Since the air is sucked from the outside by the decompression relief step of Step S2, the volume of the driving fluid filling the second space 2b, the driving flow path 53 and the cylinder 511 is larger at the time of the compression step than at the time of the decompression step. Thus, if, e.g., the plunger 512 is advanced to the reference position in the compression step, the driving fluid may be excessively compressed, causing problems such as damage on the diaphragm 3. Therefore, in case that pressure (absolute value) at the time of compression and pressure (absolute value) at the time of decompression are set to approximately the same, a travel distance of the plunger 512 needs to be smaller at the time of the compression step than at the time of the decompression step. In the present embodiment, the travel distance of the plunger 512 at the time of the compression step is smaller than that at the time of the decompression step.

In the compression relief step of Step S4, the driving fluid is released to the atmospheric pressure by opening the pressure release valve 522 in Step S41. Since pressure of the driving fluid becomes the atmospheric pressure by performing the compression relief step, the diaphragm 3 returns to the no-load position. At this time, the control unit 7 opens the inflow-side solenoid valve 6a and closes the outflow-side solenoid valve 6b so that the liquid to be fed does not flow back. In this regard, the inflow-side solenoid valve 6a may be closed. Then, the inflow-side solenoid valve 6a may be opened after driving the plunger 512 in the plunger position adjustment step of Step S5 in a closed state of the both solenoid valves 6a and 6b which are closed in the compression relief step of Step S4, or in case of repeating Step S1 again after Step S5, the inflow-side solenoid valve 6a may be opened after driving the plunger 512 in Step S1.

In the plunger position adjustment step of Step S5, the plunger 512 is advanced to the reference position (in this example, the position of the plunger 512 when fully pushed) in Step S51 and the plunger 512 is stopped in Step S52, and after that, the pressure release valve 522 is closed in Step S53. In the present embodiment, since the travel distance of the plunger 512 at the time of the compression step is smaller than that at the time of the decompression step as described above, it is necessary to return the plunger 512 to the reference position by the plunger position adjustment step. In case that pressure (absolute value) at the time of compression is set to higher than pressure (absolute value) at the time of decompression, the plunger 512 can be moved to the reference position in the compression step and the plunger position adjustment step of Step S5 can be omitted. In case that the plunger 512 is advanced beyond the reference position in the compression step, the plunger 512 should be retracted and returned to the reference position in the plunger position adjustment step.

After that, in Step S6, the control unit 7 determines whether to end the pump operation. When the determination made in Step S6 is No, the process returns to the decompression process of Step S1. When the determination made in Step S6 is Yes, the process ends. The pump operation is ended when, e.g., the output value of the pressure sensor 532 exceeds a predetermined threshold or when a termination command by an operation of a user or a program, etc., is input to the control unit 7.

Figure 4A:
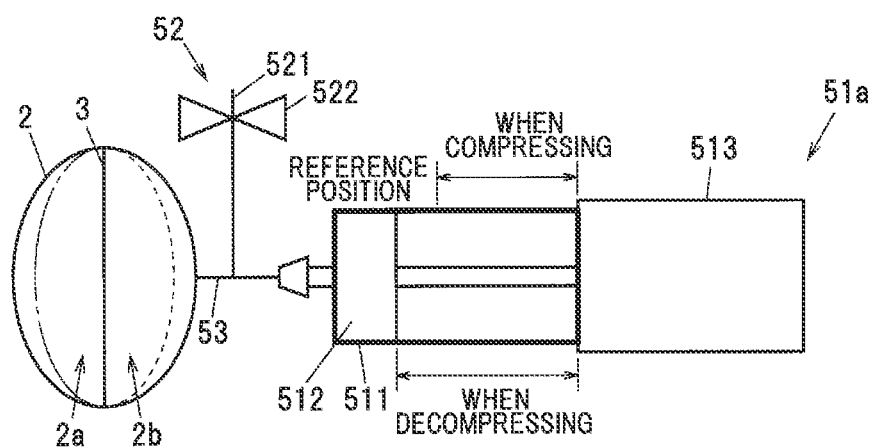
FIG. 4A is an explanatory diagram illustrating a drive range of a plunger of the invention.

In the diaphragm pump 1 of the present embodiment, after the plunger 512 is retracted in the decompression step, it is opened to atmosphere and the plunger 512 is then advanced in the compression step, hence, a travel region of the plunger 512 in the cylinder 511 when decompressing and that when compressing can be the same, as shown in FIG. 4A. Therefore, the travel distance (stroke distance) of the plunger 512 can be reduced, which contributes to size reduction of the reciprocating pump 51a and size reduction of the entire diaphragm pump 1.

Figure 4B:
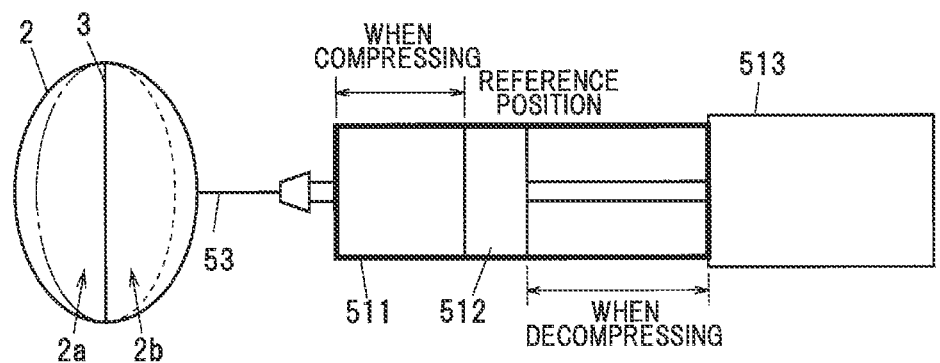
FIG. 4B is an explanatory diagram illustrating the drive range of the plunger in a conventional technique.

In contrast to this, in a conventional diaphragm pump which does not include the pressure release mechanism 52, after retracting the plunger 512 in the decompression step, pressure of the fluid to be fed and pressure of the driving fluid are balanced by advancing the plunger 512 in the compression step, and after that, the plunger 512 needs to be further advanced to compress the driving fluid, hence, the travel region of the plunger 512 in the cylinder 511 when decompressing is different from that when compressing, as shown in FIG. 4B. Therefore, in the conventional structure, the travel distance (stroke distance) of the plunger 512 is long and the size of the reciprocating pump 51a is thus large. In this regard, it is conceivable to increase a cross-sectional area of the cylinder 511 to reduce the travel distance (stroke distance) of the plunger 512, but in this case, a pressure-receiving area of the plunger 512 increases and the plunger driving part 513 which drives the plunger 512 is thus increased in size. FIGS. 4A and 4B show that the diaphragm 3 at the time of decompression moves toward a broken line and how the diaphragm 3 at the time of compression moves toward a dash-dot line.

When the diaphragm pump 1 is used as, e.g., a blood pump, blood flows through the liquid feed flow path 4 and the first space 2a, hence, it is desirable that the liquid feed flow path 4 and the case 2 be removable from the driving flow path 53 and be disposable. Even when the diaphragm pump 1 is used as another liquid feed pump, configuring the liquid feed flow path 4 and the case 2 to be removable from the driving flow path 53 and to be disposable eliminates time and effort for cleaning and improves the convenience. Furthermore, by configuring the liquid feed flow path 4 and the case 2 to be disposable, it is also possible to suppress a decrease in discharge accuracy due to deterioration over time, precipitation of calcium carbonate in the dialysate or adhesion of proteins contained in the waste dialysate. In this regard, the case 2 does not need to be entirely disposable and may be configured to be splittable on, e.g., the second space 2b side relative to the diaphragm 3 so that only a portion of the case 2 including the first space 2a can be disposable.

(Modification) Although the position of the plunger 512 when fully pushed is set as the reference position in the present embodiment, the reference position can be appropriately set. In this case, however, to return the plunger 512 to the reference position, it is necessary to provide a plunger position detection unit 514 capable of detecting that the plunger 512 is located at the reference position. As the plunger position detection unit, 514 it is possible to use, e.g., an encoder that detects a rotational speed of a motor used for the plunger driving part 513, etc., or a linear potentiometer that directly detects the position of the plunger 512, etc. In addition, when using a stepping motor (pulse motor) as the plunger driving part 513, it is possible to detect the position of the plunger 512 also based on a driving amount (a number of output pulses) of the stepping motor. Furthermore, as the plunger position detection unit, 514 it also possible to use a contact type sensor such as limit switch, strain gauge or piezoelectric element sensor and it is also possible to use a non-contact sensor such as photoelectric sensor or pressure sensor.

A diaphragm position detection unit 19 to detect a position of the diaphragm 3 may be further provided. The diaphragm position detection unit 19 may be configured to detect the position of the diaphragm 3 using, e.g., a sensor or the like such as photoelectric sensor. It is also possible to estimate the position of the diaphragm 3 by using the detection result of the encoder or linear potentiometer mentioned above, or the driving amount of the stepping motor, or an output of the pressure sensor 532. In case that the diaphragm position detection unit 19 is provided, the control unit 7 ends the decompression step when the position of the diaphragm 3 reaches a predetermined decompression position in the decompression step, and ends the compression step when the position of the diaphragm 3 reaches a predetermined compression position in the compression step.

FIG. 5 shows a control flow when the plunger position detection unit 514 and the diaphragm position detection unit 19 are provided. FIG. 5 is a modification of the control flow of FIG. 3 in which Step S12 in the decompression step of Step S1, Step S32 in the compression step of Step S3 and Step S51 of the plunger position adjustment step of Step S5 in are changed.

In case that the diaphragm position detection unit 19 is provided, in the decompression step of Step S1, the plunger 512 is retracted from the reference position in step S11, and whether the diaphragm 3 has reached a predetermined decompression position is determined in Step S12 based on the detection result or estimation result of the diaphragm position detection unit 19. When the determination made in Step S12 is No, the process returns to Step S11. When the determination made in Step S12 is Yes, the plunger 512 is stopped in Step S13.

Meanwhile, in the compression step of Step S3, the plunger 512 is advanced in Step S31, and whether the diaphragm 3 has reached a predetermined compression position is determined in Step S32 based on the detection result or estimation result of the diaphragm position detection unit 19. When the determination made in Step S32 is No, the process returns to Step S31. When the determination made in Step S32 is Yes, the plunger 512 is stopped in Step S33.

Furthermore, in the plunger position adjustment step of Step S5, the plunger 512 is advanced in Step S511, and whether the plunger 512 is located at the reference position is determined in Step S512. When the determination made in Step S512 is No, the process returns to Step S511. When the determination made in Step S512 is Yes, the plunger 512 is stopped in Step S52 and the pressure release valve 522 is then closed in Step S53.

Since the travel distance of the plunger 512 can be controlled more accurately by having the plunger position detection unit, 514 the discharge amount of the reciprocating pump 51a can be controlled with high repetition accuracy. In addition, by using the stepping motor for the plunger driving part 513, it is possible to realize the plunger position detection unit 514 without separately adding a sensor, etc., thereby contributing to the reduction in the number of components, cost reduction, and size reduction. Furthermore, when stopping the reciprocating pump 51a, the stopping process can be performed without via a sensor or the like, hence, it is possible to accurately stop the plunger 512 at a desired position without being affected by a time lag, and the discharge amount and the introduction amount of the reciprocating pump 51a can be arbitrarily set with higher accuracy.

In addition, by having the diaphragm position detection unit 19 and configuring to switch between compression and decompression according to the position of the diaphragm 3, it is possible to suppress excessive load on the diaphragm 3, to further increase safety by suppressing problems such as damage on the diaphragm 3, and to suppress deterioration of the diaphragm 3.

Furthermore, the diaphragm 3 may be configured to be naturally displaced such that the volume of the first space 2a is increased by liquid pressure of the liquid to be fed. In this case, by using, e.g., a predetermined liquid feed drive source provided on the upstream side of the inflow-side solenoid valve 6a in a state in which the pressure release valve 522 is opened, the diaphragm 3 is displaced such that the volume of the first space 2a is increased by the liquid pressure of the liquid to be fed, and the liquid to be fed thereby flows into the first space 2a. Then, by driving the compression/decompression device 51 (the reciprocating pump 51a) in a state in which the pressure release valve 522 is closed, the driving fluid is compressed and this causes the diaphragm 3 to be displaced such that the volume of the second space 2b increases, and the liquid to be fed thereby flows out of the first space 2a.

Functions and Effects of the Embodiment

As described above, in the diaphragm pump 1 of the present embodiment, the drive unit 5 has the pressure release mechanism 52 to release pressure of the driving fluid after the driving fluid is compressed or decompressed by the compression/decompression device 51 (the reciprocating pump 51a).

By having the pressure release mechanism 52, it is possible to release pressure of the driving fluid after compressing (or decompressing) the driving fluid and then quickly compress (or decompress) the driving fluid. As a result, the cycle time to decompress and compress the driving fluid, i.e., a cycle of displacement of the diaphragm 3 can be shortened, and the diaphragm pump 1 having a high flow rate can be realized.

When the pressure release mechanism 52 is not provided, the diaphragm 3 gradually returns to the no-load position with the movement of the plunger 512 after decompression or compression of the driving fluid, and the length of time that a load (tension) is applied to the diaphragm 3 is longer. By having the pressure release mechanism 52 as in the present embodiment and releasing the pressure after decompression or compression of the driving fluid, it is possible to reduce the length of time that a load (tension) is applied to the diaphragm 3 since the diaphragm 3 instantaneously returns to the no-load position. That is, according to the present embodiment, it is possible to reduce damage on the diaphragm 3 and possible to realize a long-life diaphragm pump 1.

Furthermore, when the pressure release mechanism 52 is not provided, the driving fluid is sealed in. Therefore, in case that air is used as the driving fluid, the air expands or contracts due to an influence of temperature, and intended displacement of the diaphragm 3 may not be obtained even if the plunger 512 is operated with the same stroke, resulting in variation in the liquid feed amount. In addition, when the driving fluid becomes hot and expands, a large load may be applied to the diaphragm 3, causing damage on the diaphragm 3. According to the present embodiment, by releasing the pressure every time the driving fluid is compressed or decompressed, it is possible to eliminate the influence of temperature of the driving fluid, to suppress problems such as damage on the diaphragm 3, and to accurately control the liquid feed amount.

Furthermore, in the present embodiment, when the reciprocating pump 51a is used as the compression/decompression device 51, the compression/decompression device 51 can be reduced in size by reducing the travel distance (stroke distance) of the plunger 512. In addition, by using the reciprocating pump 51*a* as the compression/decompression device 51, it is possible to realize the diaphragm pump 1 with less vibration and less operating sound than general compressors, etc.

SUMMARY OF THE EMBODIMENT

Technical ideas understood from the embodiment will be described below citing the reference numerals, etc., used for the embodiment. However, each reference numeral, etc., described below is not intended to limit the constituent elements in the claims to the members, etc., specifically described in the embodiment.

[1] A diaphragm pump (1) comprising: a case (2); a diaphragm (3) dividing a space in the case (2) into a first space (2*a*) and a second space (2*b*); a liquid feed flow path (4) comprising an inflow path (4*a*) to introduce a liquid to be fed into the first space (2*a*) and an outflow path (4*b*) to discharge the liquid to be fed from the first space (2*a*); a drive unit (5) comprising a compression/decompression device (51) that repeatedly causes displacement of the diaphragm (3) by repeating compression and decompression of a driving fluid filling the second space (2*b*); and a valve mechanism (6) to open and close the inflow path (4*a*) and the outflow path (4*b*), wherein the drive unit (5) comprises a pressure release mechanism (52) to release pressure of the driving fluid after the driving fluid is compressed or decompressed by the compression/decompression device (51).

[2] The diaphragm pump (1) described in [1], comprising: a control unit (7) that controls the compression/decompression device (51) and the pressure release mechanism (52), wherein the control unit (7) repeatedly performs a decompression step of decompressing the driving fluid by the compression/decompression device (51), a decompression relief step of releasing the pressure of the driving fluid by the pressure release mechanism (52), a compression step of compressing the driving fluid by the compression/decompression device (51), and a compression relief step of releasing the pressure of the driving fluid by the pressure release mechanism (52).

[3] The diaphragm pump (1) described in [2], wherein the compression/decompression device (51) comprises a reciprocating pump (51*a*) that comprises a cylinder (511) in communication with the second space (2*b*), a plunger (512) provided so as to be able to advance and retract within the cylinder (511), and a plunger driving part (513) to advance and retract the plunger (512), and compresses and decompresses the driving fluid by advancing and retracting the plunger (512) within the cylinder (511) by the plunger driving part (513).

[4] The diaphragm pump (1) described in [3], wherein the control unit (7) is configured to decompress the driving fluid by retracting the plunger (512) from a reference position in the decompression step, and performs a plunger position adjustment step of moving the plunger (512) to the reference position after the compression relief step.

[5] The diaphragm pump (1) described in [4], comprising: a plunger position detection unit capable of detecting that the plunger (512) is located at the reference position.

[6] The diaphragm pump (1) described in any one of [2] to [5], comprising: a diaphragm position detection unit 19 to detect a position of the diaphragm (3), wherein the control unit (7) ends the decompression step when the position of the diaphragm (3) reaches a predetermined decompression position in the decompression step, and ends the compression step when the position of the diaphragm (3) reaches a predetermined compression position in the compression step.

[7] The diaphragm pump (1) described in any one of [1] to [6], wherein the driving fluid comprises air, and wherein the pressure release mechanism (52) comprises a pressure release flow path (521) with one end in communication with the second space (2*b*) and the other end opened to the atmosphere, and a pressure release valve (522) provided on the pressure release flow path (521) to open/close the pressure release flow path (521).

[8] The diaphragm pump (1) described in any one of [1] to [7], comprising: a socket part (24) to which the drive unit (5) is connected, wherein the case (2) and the diaphragm (3) are provided so as to be removable from the socket part (24).

[9] A blood purification apparatus (10), comprising: the diaphragm pump (1) described in any one of [1] to [7] as at least one of liquid feed pumps provided on a blood circuit (11) to extracorporeally circulate blood of a patient, a liquid supply flow path (13) to supply a supply liquid to the blood circuit (11) or to a blood purifier (12) provided on the blood circuit (11), and a waste liquid flow path (14) to discharge a waste liquid from the blood purifier (12).

Although the embodiment of the invention has been described, the invention according to claims is not to be limited to the embodiment described above. In addition, not all combinations of the features described in the embodiment are necessary to solve the problem of the invention.

The invention can be appropriately modified and implemented without departing from the gist thereof. For example, although the example in which the valve mechanism 6 is composed of a solenoid valve has been described in the embodiment, the valve mechanism 6 may be composed of a check valve.

REFERENCE SIGNS LIST

1 diaphragm pump
2 case
2*a* first space
2*b* second space
3 diaphragm
4 liquid feed flow path
4*a* inflow path
4*b* outflow path
5 drive unit
51 compression/decompression device
51*a* reciprocating pump
511 cylinder
512 plunger
513 plunger driving part
52 pressure release mechanism
521 pressure release flow path
522 pressure release valve
53 driving flow path
531 air filter
532 pressure sensor
6 valve mechanism
6*a* inflow-side solenoid valve
6*b* outflow-side solenoid valve
7 control unit
10 blood purification apparatus
11 blood circuit
111 blood pump
112 gas-liquid separator
12 blood purifier 13 liquid supply flow path
13a dialysate flow path
14 waste liquid flow path
14a water removal flow path
151 undiluted fluid storage tank
152 undiluted fluid flow path
153 undiluted fluid injection pump
16 duplex pump
17 water removal pump
19 diaphragm position detection unit
514 plunger position detection unit

The invention claimed is:

1. A diaphragm pump, comprising:
a case;
a diaphragm dividing a space in the case into a first space and a second space;
a liquid feed flow path comprising an inflow path to introduce a liquid to be fed into the first space and an outflow path to discharge the liquid to be fed from the first space;
a drive unit comprising:
  a compression/decompression device that repeatedly causes displacement of the diaphragm by repeating compression and decompression of a driving fluid filling the second space, wherein the compression/decompression device comprises:
    a reciprocating pump that comprises a cylinder in communication with the second space,
    a plunger provided so as to be able to advance and retract within the cylinder, and
    a plunger driving part to advance and retract the plunger, and compresses and decompresses the driving fluid by advancing and retracting the plunger within the cylinder by the plunger driving part, and
  a pressure release mechanism to release pressure of the driving fluid after the driving fluid is compressed or decompressed by the compression/decompression device;
a control unit that controls the compression/decompression device and the pressure release mechanism; and
a valve mechanism to open and close the inflow path and the outflow path,
wherein the control unit repeatedly performs a decompression step of decompressing the driving fluid by retracting the plunger from a reference position which is the position where the plunger is fully pushed in the cylinder and introducing the liquid to be fed into the first space from the inflow path, a decompression relief step of releasing the pressure of the driving fluid by the pressure release mechanism, a compression step of compressing the driving fluid by advancing the plunger towards the reference position to discharge the liquid to be fed in the first space to the outflow path and stopping at a position before reaching the reference position, a compression relief step of releasing the pressure of the driving fluid by the pressure release mechanism, and a plunger position adjustment step of moving the plunger from the position before reaching the reference position to the reference position after the compression relief step.

2. The diaphragm pump according to claim 1, comprising:
a plunger position detection unit capable of detecting that the plunger is located at the reference position.

3. The diaphragm pump according to claim 1, comprising:
a diaphragm position detection unit to detect a position of the diaphragm,
wherein the control unit ends the decompression step when the position of the diaphragm reaches a predetermined decompression position in the decompression step, and ends the compression step when the position of the diaphragm reaches a predetermined compression position in the compression step.

4. The diaphragm pump according to claim 1, wherein the driving fluid comprises air, and wherein the pressure release mechanism comprises a pressure release flow path with one end in communication with the second space and the other end opened to the atmosphere, and a pressure release valve provided on the pressure release flow path to open/close the pressure release flow path.

5. The diaphragm pump according to claim 1, comprising:
a socket part to which the drive unit is connected,
wherein the case and the diaphragm are provided so as to be removable from the socket part.

6. A blood purification apparatus, comprising:
the diaphragm pump according to claim 1 at least one liquid feed pump provided on a blood circuit to extracorporeally circulate blood of a patient, a liquid supply flow path to supply a supply liquid to the blood circuit or to a blood purifier provided on the blood circuit, and a waste liquid flow path to discharge a waste liquid from the blood purifier.

7. The diaphragm pump according to claim 1, wherein a compression travel distance of the plunger during the compression step is smaller than a decompression travel distance of the plunger during the decompression step.

* * * * *